United States Patent [19]

Daviduk et al.

[11] 4,251,484
[45] Feb. 17, 1981

[54] METHOD AND APPARATUS FOR CONVERTING ALCOHOLS TO HYDROCARBONS

[75] Inventors: Nicholas Daviduk, Pennington; James H. Haddad, Princeton Junction, both of N.J.

[73] Assignee: Mobil Oil Corporation, N.Y.

[21] Appl. No.: 89,705

[22] Filed: Oct. 30, 1979

[51] Int. Cl.³ .............................. B01J 8/20; B01J 8/24
[52] U.S. Cl. ...................................... 422/145; 422/49; 422/140; 422/143; 422/146; 422/147
[58] Field of Search ................. 422/146, 147, 49, 140, 422/143, 145

[56] References Cited

U.S. PATENT DOCUMENTS

| | | | |
|---|---|---|---|
| 2,518,270 | 8/1950 | Barr | 422/146 |
| 2,620,262 | 12/1952 | Hujsak | 422/146 |
| 2,627,522 | 2/1953 | Krebs et al. | 422/146 X |
| 2,852,545 | 9/1958 | Jenny | 422/146 X |
| 2,886,419 | 5/1959 | Orr et al. | 422/147 X |
| 2,931,711 | 4/1960 | Walker | 422/146 |
| 3,226,204 | 12/1965 | Statler | 422/146 X |

*Primary Examiner*—Barry Richman
*Attorney, Agent, or Firm*—Charles A. Huggett; Ronald J. Cier

[57] ABSTRACT

Apparatus and method of utilization for controlling exothermic reactions such as the conversion of methanol to hydrocarbons are discussed. More particularly, the arrangement of apparatus comprising heat exchange tubes and open end baffle tubes for maintaining the hydraulic diameter within restricted limits during contact between vaporous reactant and a fluid bed of catalyst is discussed.

5 Claims, 3 Drawing Figures

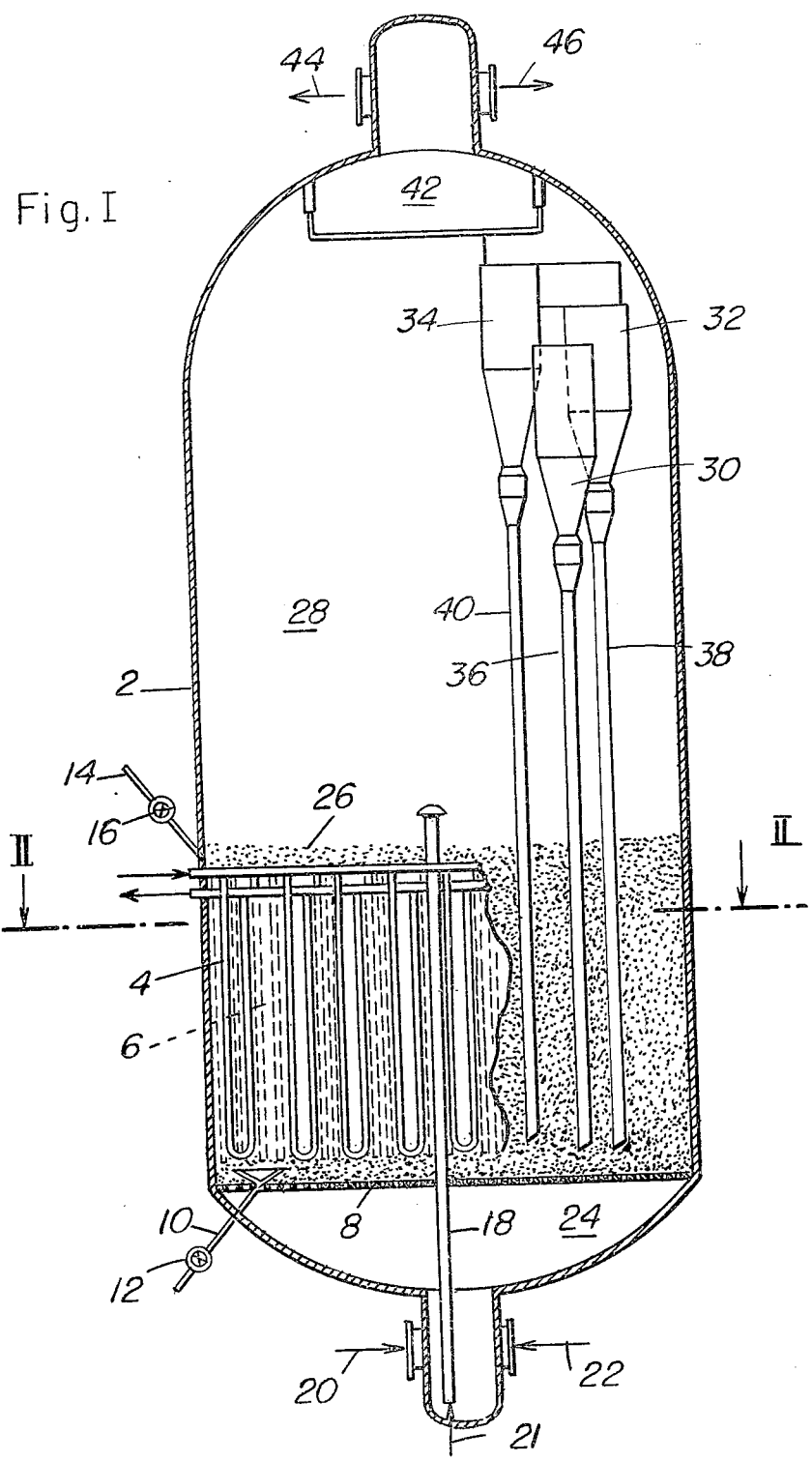
Fig. I

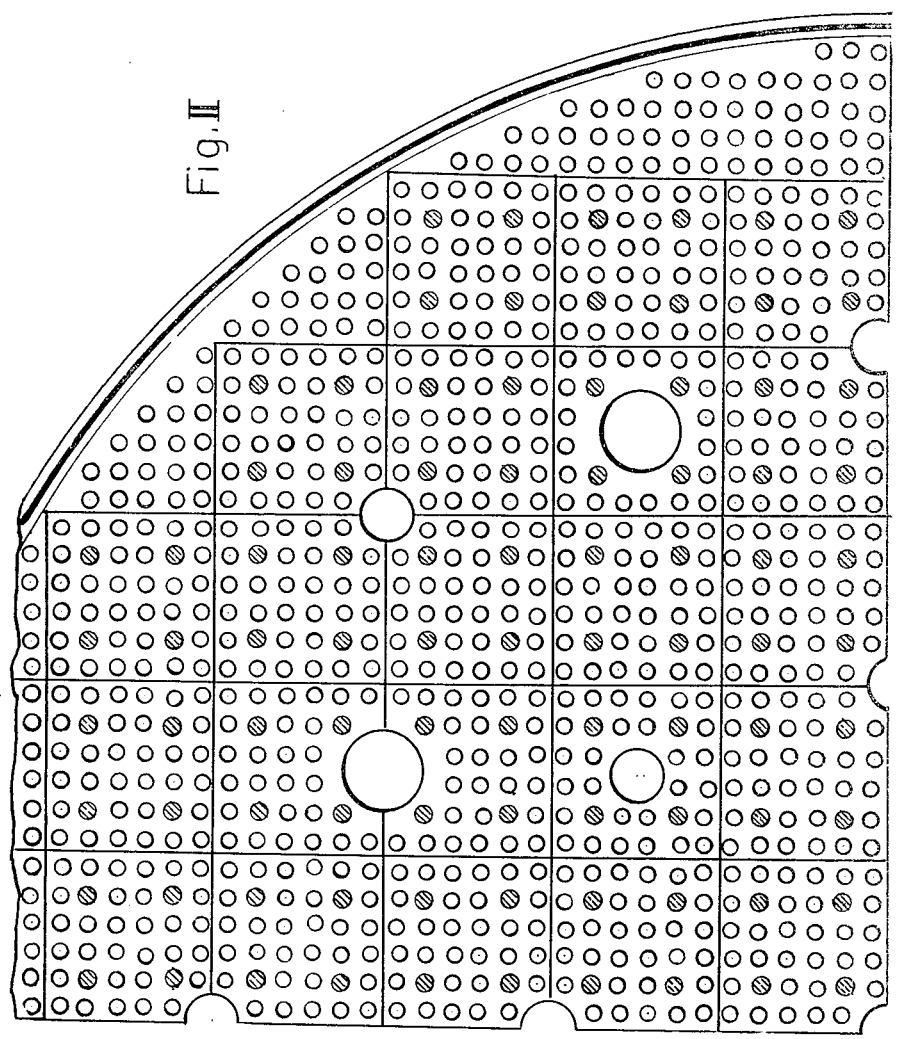
Fig. II
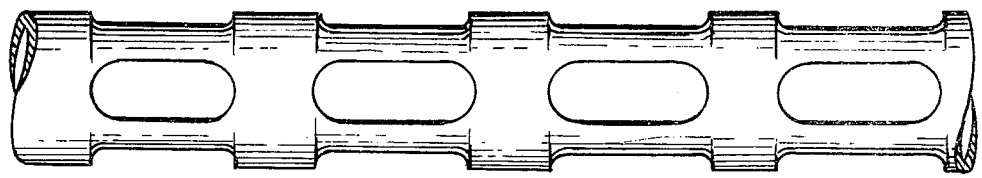
Fig. III

4,251,484

METHOD AND APPARATUS FOR CONVERTING ALCOHOLS TO HYDROCARBONS

BACKGROUND OF THE INVENTION

The application of fluidized catalyst techniques for effecting chemical reactions embodying the distribution of heat and/or the disposal of undesired reaction heat has long been accepted as a major processing tool of the petroleum and chemical industry. For example, it has been proposed to use the fluidized catalyst technique in the exothermic reactions of Fischer-Tropsch synthesis, the known Oxo process as well as others for the disposal of generated heat. In the fluid catalytic cracking of hydrocarbons, the fluid catalyst conveys heat generated in the catalyst regeneration zone to the hydrocarbon conversion zone wherein the conveyed heat is given up by converting hydrocarbons admixed therewith to form more desirable hydrocarbon products such as gasoline. In these various fluidized catalyst operations, disposal of the reaction heat has been accomplished by different techniques including the transfer of heat to cooling coils, and indirect heat exchange with fluidized catalyst particles or reactant feed streams and product streams.

The conversion of lower alcohols, such as methanol, to intermediate ether products followed by conversion of the ether product to one or a combination of products comprising olefins and/or aromatics has been the subject of several patents. Such patents include U.S. Pat. Nos. 3,928,483; 3,931,349; 3,969,426; 3,998,899; 4,013,732; 4,035,430; 4,044,061; 4,046,825; 4,052,479; 4,058,576; 4,062,905; 4,071,573; 4,076,761; 4,118,431 and 4,138,440. These patents and others have been considered in the preparation of this application.

Some other patents given consideration include U.S. Pat. Nos. 2,493,526; 2,571,380; 2,627,522; 2,920,940 and 3,151,944.

SUMMARY OF THE INVENTION

This invention relates to an arrangement of apparatus and its method of utilization for effecting the conversion of lower alcohols such as methanol, ethanol, and propanol, ether derivatives thereof and mixtures of alcohols and ethers in the presence of fluid catalyst particles of a special class of crystalline zeolites to form hydrocarbons including gasoline boiling range hydrocarbons characterized as olefinic and/or aromatic hydrocarbons.

More particularly, the present invention is directed to an arrangement of apparatus for effecting the conversion of methanol in the presence of fluid catalyst particles comprising a special zeolite characterized as providing a pore opening of at least 5 Angstroms, a silica/alumina ratio of at least 12 and a Constraint Index within the range of 1 to 12. The arrangement of apparatus comprises in combination a cylindrical reactor housing a generally upflowing fluidized relatively dense mass of catalyst particles initially contacted by vapor and/or liquid lower alcohols, ether derivatives thereof and related oxygenates or a mixture thereof. The charge may be methanol alone, in admixture with ether (DME) and related oxygenates including oxygenates of Fischer-Tropsch synthesis.

The reactor is provided with a plurality of vertically arranged steam generation tubes in combination with juxtapositioned special gas bubble dispersing baffle tubes confined particularly within the most dense portion of the fluid mass of catalyst particles within the lower portion of the reactor. A catalyst regenerator is provided adjacent the reactor in combination with associated subsystems provided for preheating the methanol feed, reactor effluent cooling and recovery, a catalyst regeneration system, a system for effecting heat-up of the reactor and related piping means between vessels which are straight or semicircular conduit means for conveying catalyst particles between the reactor and the regenerator. The steam tubes and the baffle tubes above mentioned for restricting gas bubble growth means which are in a specific embodiment, 4 inch nominal diameter tubes hung vertically from support beams. The baffle tubes are open at the top and bottom. They are provided with a plurality of staggered elongated slots in the wall of the baffle tube at spread apart intervals to permit the transfer of catalyst particles and vaporous material into and through the slots in the baffle tubes without substantial flow restriction except to suppress gas bubble growth. A sufficient number of vertical steam tubes and baffle tubes are arranged adjacent to one another in the fluid mass of catalyst particles to provide an equivalent hydraulic diameter between catalyst particles and vaporous material restricted to within the range of 4 to 8 inches and preferably to about 6 inches. In one specific embodiment of the apparatus arrangement herein described, it is contemplated utilizing a catalyst inventory for the reactor and regenerator arrangement of about 933,000 pounds based on a reactor size providing a catalyst bed depth of about 40 feet in a 35 foot diameter reactor. It is also contemplated using a catalyst bed depth less than 40 feet, such as 20 or 30 feet. The specific apparatus arrangement and size herein described are designed for processing about 52,640 BPD of crude distilled methanol containing up to about 4% water and producing, under the selected operating conditions, about 13,400 BPD of $C_5+$ gasoline boiling range products plus light olefins, paraffins, isoparaffins and naphthenes as secondary products. Alkylation of olefinic secondary products may be accomplished in separate equipment known in the art.

The crystalline zeolites utilized herein are members of a novel class of zeolitic materials which exhibit unusual properties. Although these zeolites have unusually low alumina contents, i.e. high silica to alumina mole ratios, they are very active even when the silica to alumina mole ratio exceeds 30. The activity is surprising, since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this novel class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred in some applications to use zeolites having higher silica/alumina ratios of at least about 30. In addition, zeolites as otherwise characterized herein but which are substantially free of aluminum, i.e. having silica to alumina mole ratios of 1,600 and higher, are found to be useful and even preferable in some instances. Such "high silica" zeolites are intended to be included within this description. The novel class of zeolites, after activation, acquire an intracrystalline sorption capacity for normal hexane which is greater than that for water, i.e. they exhibit "hydrophobic" properties. This hydrophobic character can be used to advantage in some applications.

The novel class of zeolites useful herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons and, therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than 1, such as 0.1 or less, can be employed in order to achieve a minimum total conversion of about 10%.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (C.I.) values for some typical materials are:

|  | C.I. |
| --- | --- |
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| TMA Offretite | 3.7 |
| Clinoptilolite | 3.4 |
| Beta | 0.6 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the Constraint Index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined novel class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than an exclusive value. That is, a base crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions, may give a Constraint Index value outside of the range of 1 to 12.

The novel class of zeolites defined herein is exemplified by ZSM-5, ZSM-11, ZSM-12, ZSM-23, ZSM-35, ZSM-38, and other similar materials.

ZSM-5 is described in greater detail in U.S. Pat. Nos. 3,702,886 and 3,941,871. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed catalyst, is incorporated herein by reference.

ZSM-35 is described in U.S. Pat. No. 4,016,245. The description of that catalyst, and particularly the X-ray diffraction pattern thereof, is incorporated herein by reference.

ZSM-38 is more particularly described in U.S. Pat. No. 4,046,859. The description of that catalyst, and particularly the specified X-ray diffraction pattern thereof, is incorporated herein by reference.

It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica/alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intracrystalline free space is occupied by organic cations from the forming solution. They may be activated by heating in an inert atmosphere at 540° C. for 1 hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35 and ZSM-38, with ZSM-5 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article ZEOLITE STRUCTURE by W. M. Meier. This paper, the entire contents of which are incorporated herein by reference, is included in PROCEEDINGS OF THE CONFERENCE ON MOLECULAR SIEVES (London, April 1967), published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
|---|---|---|
| Ferrierite | 0.28 cc/cc | 1.76 g/cc |
| Mordenite | .28 | 1.7 |

-continued

|  | Void Volume | Framework Density |
|---|---|---|
| ZSM-5, −11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5% by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing a particularly desired chemical conversion process, it may be useful to incorporate the above-described crystalline zeolite with a matrix comprising another material resistant to the temperature and other conditions employed in the process. Such matrix material is useful as a binder and imparts greater resistance to the catalyst for the severe temperature, pressure and reactant feed stream velocity conditions encountered in many cracking processes.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely, with the zeolite content ranging from between about 1 to about 99% by weight and more usually in the range of about 5 to about 80% by weight of the dry composite.

In the reactor arrangement herein described, the heat of reaction obtained by converting the methanol charge is absorbed by the catalyst and in substantial measure by the steam tubes to produce 600 psig steam. This arrangement is intended to restrict the temperature to about 600° F. at the bottom of the bed and the fluid bed upper interface to within the range of 750° F. to about 775° F. Preferably the temperature in the reactor dilute phase is about 765° F. In this methanol conversion and operating environment, it is contemplated achieving a methanol conversion of greater than 95% and preferably about 99.5% to minimize the loss of difficult to recover methanol in process formed water. At the operating conditions defined, including a pressure restriction of about 32 psig at the bottom of the fluid mass of catalyst and about 25 psig in the reactor dispersed catalyst phase and relying upon a nominal gas velocity of about 2 ft./sec., the density of the fluid mass of catalyst in the lower portion of the reactor is about 27 lbs/cu.ft. However, changes in gas velocity can change the bed density to higher and lower values. That is, when it is desired to change product selectivity to one of high olefin content as opposed to high aromatics yield, the reaction time as a function of space velocity may be reduced by increasing the space velocity. On the other hand, aromatic formation is enhanced by a reduction in reactant space velocity to increase time of contact between methanol reactant product and catalyst. A good balance in product selectivity between olefins, aromatics and paraffins may be had by a proper selection of reaction conditions.

It is known that large gas bubbles can form in a fluid catalyst system and particularly large diameter, deep, fluidized catalyst beds even if the gas is first injected into the bed in an atomized condition or as very small gas bubbles. It is believed that, to achieve the high methanol conversion desired, above 95%, it is essential to severely restrict gas bubble growth to less than 24 inches, and preferably not to exceed about 8 inches. More preferably, the hydraulic diameter of the reactor or system should be restricted to within the range of 4 to 8 inches when charging liquid or vaporized methanol for contact with the catalyst at the bottom of the fluid bed of catalyst above a distributor grid. To provide the hydraulic restrictions particularly preferred herein, the steam tubes are located vertically within the reactor, in a plurality of separate flow controlled bundles of tubes which can be shut off or separately removed and replaced as required in the event of any malfunctions. Thus, the steam tubes are vertically hung resembling bayonet type heat exchange tubes attached to separate plenum chambers at the top for adding water and removing high pressure steam respectively. In addition to the vertical steam tubes, a plurality of vertical baffle tubes are provided therebetween which permit the free upflow of catalyst, reactants and reaction products while maintaining the reactor hydraulics as herein provided. The baffle tubes and the steam tubes are arranged uniformly over the reactor cross-section in a particular grid pattern or arrangement compatible with obtaining desired heat transfer, restriction of gas bubble growth and provide for recycling centrifugally separated catalyst by diplegs provided to various bed sections such as a bottom, intermediate and/or upper portion of the most dense fluid mass of catalyst in the reactor zone. It is preferred to discharge all dipleg catalyst adjacent the bottom of the bed. The reactor is provided with eight sets of three stage cyclones, in which arrangement all of the diplegs return separated catalyst to a bottom portion of the fluid bed. In addition, the portion of the vessel housing the cyclones may be larger in diameter than that portion of the vessel housing the most dense fluid bed of catalyst and the heat exchange tubes. Such enlargement by reducing reactant velocity will operate to also reduce catalyst entrainment into the cyclones.

The most dense bed of catalyst in the reactor vessel is supported above a horizontal reactant inlet distributor grid perforated by a multiplicity of small diameter holes, about 11,000, providing relatively uniform dispersal of vaporous and/or liquid methanol feed depending on preheat at the bottom of the fluid bed of catalyst. In one particular arrangement, the small diameter feed inlet holes are about 0.25 inch in diameter. The pressure drop across the grid is sufficiently high to insure uniform distribution of feed gas. It is contemplated providing an open ended catalyst transfer tube extending from beneath the feed inlet distributor grid into the dispersed phase above the more dense fluid bed of catalyst. The top end of this open ended tube may be covered by a spaced apart inverted dish shaped plate to inhibit catalyst particles from falling down into the tube. The bottom end of this catalyst transfer tube extends to a low point of the reactor vessel beneath the grid and is provided with nozzle means for injecting a fluidizing gas for conveying catalyst particles falling through the grid during shutdown and before start-up from beneath the grid into the catalyst system above the grid. Thus it is contemplated fluidizing the mass of catalyst passed to the reactor and in the reactor with an inert gas such as nitrogen or other material suitable for the purpose to clear the chamber in the reactor beneath the grid of catalyst and to fluidize the catalyst bed before injecting the methanol comprising charge under selected reaction conditions.

It will be quite apparent from the discussion herein presented that the arrangement of apparatus and the method of utilizing such apparatus are designed to accomplish dehydration of the alcohol charge to its corresponding ether and effect conversion thereof to at least olefins and/or aromatics. It is generally preferred, however, that the operation be performed under conditions restricting the formation of durene. However, formation of some durene (1, 2, 4, 5 tetramethyl benzene) is not fatally restricting to the process. This can be restricted by limiting contact between formed aromatics and methanol charged.

In a reactor system particularly identified and its operation as herein identified, there is a large circulation of catalysts in the most dense fluid catalyst bed, in the dispersed catalyst phase, between the dense and dispersed catalyst phases, as well as from the catalyst phases through the cyclones and return to the lower portion of the catalyst bed by the cyclone diplegs. It is contemplated circulating from about 4 to 8 million pounds per hour of catalyst in the specifically identified apparatus of this invention; the major portion of the cyclone separated catalyst flows through the diplegs of the first stage cyclones of which there are eight in the specific apparatus embodiment. The circulated catalyst will accumulate carbonaceous deposits thereon of a relatively high order of magnitude, since only a portion of this circulated catalyst is withdrawn for passage to catalyst regeneration for burning a portion of the deposited carbonaceous material in a separate temperature restricted catalyst regeneration zone. In the methanol conversion apparatus arrangement, it is contemplated maintaining a high coke level on internally circulated catalyst to preferentially promote the product of olefins and/or aromatics and isoparaffins. Thus the level of coke like material (hydrocarbonaceous) retained on the catalyst may be within the range of 5 to 20% by weight and more preferably within the range of 10 to 15% by weight. When operating to produce preferably olefinic components, the olefins produced may be cyclized in a separate downstream zone free of methanol, thereby permitting minimizing the tendency to produce aromatics higher boiling than gasoline boiling components.

FIG. I is a diagrammatic sketch in elevation of the reactor apparatus of this invention comprising an arrangement of heat exchange tubes and baffle tubes positioned in a lower portion of the reactor vessel and spaced vertically above a distributor grid means.

FIG. II is a diagrammatic sketch of a portion of cross-section A—A of FIG. I, showing the relationship between heat exchange tubes, baffle tubes and cyclone diplegs.

FIG. III is a view of a portion of the open end baffle tube showing the arrangement for slotting the tube wall.

Referring now to FIG. I by way of example, a reactor vessel 2 is shown provided with heat exchange tube means 4 and baffle tube means 6. The arrangement of these tube means with respect to one another is more clearly shown by the cross-sectional view and arrangement of FIG. II. Furthermore, it is to be understood that there are several separate heat exchange steam generating tube bundles so that temperature control can be separately exercised over different portions of the fluid catalyst bed. The bottoms of the tubes are spaced above a feed distributor grid 8 approximately 2 feet in a specific arrangement and sufficiently above the grid to be free of jet action by the charged feed through the small diameter holes in the grid. As mentioned above, the holes in the grid are 0.25 inch in diameter, and in one specific arrangement there are approximately 11,000 holes. Provision is made for withdrawing catalyst from above grid 8 as by conduit means 10 provided with flow control valve 12 for passage to catalyst regeneration not shown. Provision is also made for passing the partially regenerated catalyst to the reactor fluid bed of catalyst as by conduit means 14 provided with flow control valve 16. The regenerated catalyst is charged to the catalyst bed beneath the upper interface and sufficiently below to achieve good mixing in the fluid bed. Since the amount of regenerated catalyst passed to the reactor is small by comparison, the temperature of the regenerated catalyst does not upset the temperature constraints of the reactor operations in a significant amount.

The reactor arrangement of the invention is provided as mentioned above with conduit means 18 such as a riser conduit for removing catalyst from a bottom portion of the vessel beneath grid 8 to an upper portion of the vessel for discharge above the bed upper dense phase interface as shown. Conduit means 21 is provided for charging an inert gas such as nitrogen for use as lift gas for removing catalyst particles by passing a suspension thereof upwardly through riser 18. The top of the riser is capped, for example, by a dish shaped baffle as shown to reduce flow of catalyst down through the riser. Conduit 21 may comprise a vertically moving plug type valve at the bottom inlet which will be closed when charging methanol to the chamber beneath grid 8.

The methanol feed with or without nitrogen or another appropriate diluent may be charged through one or more openings 20 and 22 in a bottom extended portion of the reactor. The methanol in liquid condition can be sprayed by suitable means into the bed above the grid. The charged methanol feed in vaporous condition enters the vessel by inlet means 20 and 22 in open communication with chamber 24 beneath grid 8. The charged methanol passes through reactant distributor grid 8 and into the bed of catalyst thereabove at a velocity sufficient to form a generally upwardly flowing suspension of reactant and reaction product with the catalyst particles. The suspended catalyst in a concentration generally less than 35 lbs/cu.ft. and about 27 lbs/cu.ft. in a specific arrangement is in random fluid movement in the bed by upflowing gasiform material, with a substantial portion thereof moving generally upward with the gasiform product material into a more dispersed catalyst phase 28 above catalyst bed interface 26.

A plurality of sequentially connected cyclone separator means 30, 32 and 34 provided with diplegs 36, 38 and 40 respectively are positioned in an upper portion of the reactor vessel comprising dispersed catalyst phase 28. In a specific arrangement, there are eight sets of three stage cyclone separating means providing in an upper portion of the reactor vessel. As shown by FIG. II, provision is made for extending the cyclone diplegs into the dense fluid bed of catalyst and preferably to a bottom portion of the fluid bed for discharge in a vertical space between grid 8 and the bottom of tubes 4 and 6 within the bed of about 2 feet. Thus in the reactor arrangement of this invention and the proposed method of utilization for converting methanol to hydrocarbons comprising olefins, aromatics, paraffins and naphthenes, the operation contemplates a high circulation rate of catalyst within the reactor vessel. In a specific example, the reactor catalyst inventory is about 878,500 pounds, and from about 4 to 8 million pounds per hour of catalyst are circulated primarily through the cyclones. In conjunction with this high catalyst circulation operation, it is contemplated maintaining the following specific reactor operating conditions:

| | |
|---|---|
| Feed to Grid 8 | |
| Methanol, mph | 19,785 |
| Recycle gas, mph | 1,522 |
| Condition below Grid 8 | |
| Temperature, °F. | 350 |
| Pressure, psig | 34.5 |
| Condition above Grid | |
| Temperature, °F. | 765 |
| Pressure, psig | 32.2 |
| Fluidized Catalyst Bed Depth, ft. | 40 |
| Fluidized Catalyst Bed Density, lbs/cu.ft. | 27 |
| Fluidized Bed Pressure Drop, psi | 7.5 |

The product effluent of methanol conversion separated from catalyst particles in the cyclone separating system then passes to a plenum chamber 42 before withdrawal therefrom by one or more opening means 44 and 46. The product effluent recovered by openings 44 and 46 is cooled and separated in means not shown to recover liquid hydrocarbons, gaseous material and formed water comprising some catalyst fines. Since conversion of the methanol is at least 95% and preferably at least 99%, the water phase with unreacted methanol is not processed for economic reasons to recover unreacted methanol. The recovered hydrocarbon product comprising olefins and/or aromatics, paraffins and naphthenes is thereafter processed as required to provide a desired gasoline or higher boiling product. In the event the reaction conditions selected produce considerable materials higher boiling than gasoline such as a light fuel oil, the higher boiling material is separated from the gasoline product for further use as desired. Light gaseous hydrocarbon products of the process may be processed as by alkylation, olefination and other known processes to produce gasoline boiling components, LPG, etc.

The total catalyst inventory for the reactor and regenerator (not shown) is about 933,000 pounds based on a 40 foot catalyst bed depth in the reactor. Therefore the regenerator catalyst inventory is about 54,500 pounds in a specific embodiment. The catalyst regenerator contemplated for use with the reactor system of this invention can be substantially any arrangement suitable for the purpose and consistant with providing a low temperature regeneration of the catalyst below 1000° F. to effect only partial coke removal by burning. Thus a dense fluid catalyst bed regeneration system may be successfully employed. The density of the regenerator fluid bed of catalyst may be the same as, slightly higher or lower than, the reactor bed density. Generally it will be about 27 lbs/cu.ft. or slightly higher to provide a proper pressure balanced system. In order to restrict the coke burning operation within limits desired, the top of the dense bed is preferably restricted not to exceed a temperature of about 900° F. and the regenerated catalyst outlet temperature preferably should not exceed about 950° F. The pressure within the regenerator is preferably about 29.9 psig at the base of the fluid bed of catalyst in the bottom portion of the regenerator. A catalyst bed depth of about 30 feet is proposed for this specific operation. The incompletely regenerated catalyst particles carrying a high level of coke thereon are recovered from the catalyst regeneration operation not shown and returned to the methanol conversion reactor at a restricted temperature by conduit 14.

Important aspects of the methanol conversion reactor herein described are manifold, since they include (1) restricting the exothermic temperature generated within relatively narrow limits; (2) restricting the reactant vapor bubble growth and thus the hydraulic diameter of the operation within particular limits; (3) maintaining a catalyst condition particularly promoting the formation of olefins and/or aromatics, paraffins, and naphthenes depending on feed composition comprising methanol; (4) maintaining a reaction condition promoting greater than 95% conversion of the methanol charge to more desirable products because of economic consideration as well as product consideration; and (5) maintaining a catalyst circulation system within operating restrictions above identified and particularly promoting the conversion of methanol to olefinic and/or aromatic gasoline boiling components.

One of the more important aspects above identified is concerned with the removal of exothermic heat and restricting the vaporous reactant hydraulic diameter. FIG. II identifies a cross-sectional view A—A of the apparatus of FIG. I having a particular bearing on these important aspects. That is, FIG. II shows the systematic relationship between vertically positioned steam tubes 50 shown as black dots with baffle tubes 52 at each cross mark to achieve the desired heat exchange and maintain a desired reactant hydraulic diameter or gas bubble growth restriction. FIG. II also shows the arrangement of cyclone standpipes 54, 56, 58, 60, 62, 64, 66, 68 and 70 provided for accomplishing the catalyst circulation desired. In each quarter section of the reactor cross-sectional area, there are at least six standpipes for returning cyclone separated catalyst to the fluid bed of catalyst. In addition, the 4 inch diameter tubes, comprising steam tubes and baffle tubes, are spaced on a grid pattern of 6 inch square or pitch which are grouped into 36 inch square bundles, each typically containing 4 steam tubes and 32 baffle tubes. In the reactor design of this invention, there are 352 steam tubes and 3,192 baffle tubes. The hydraulic diameter of each 36 inch square tube bundle is about 5.3 inches when using 4.5 in O.D. tubes in a specific arrangement. However, the hydraulic diameter of the reactor is about 6 inches.

The baffle tubes 52 used in the apparatus are particularly shown in partial view in FIG. III. These baffle tubes 52 confined with the dense fluid bed of catalyst as herein provided are open ended tubes, about 4 inches in diameter or 4.5 inch O.D. tubes, and slotted in the wall as shown to provide approximately 2×4 inch slots to permit ingress and egress of catalyst particles and vaporous material within the bubble breaking constraints of this invention. For a baffle tube of 4 inch diameter, the slots are generally round on each end and arranged in a pattern in the tube wall throughout a major portion of its length.

FIGS. II and III are believed to be generally self-explanatory when considered in the light of the discussion above and minor deviations therefrom are considered to be within the scope of the invention.

Having thus generally described the method and apparatus of this invention and described specific examples in support thereof, it is to be understood that no undue restrictions are to be imposed by reasons thereof except as defined by the following claims.

We claim:

1. An apparatus for converting lower alcohols to hydrocarbons including gasoline boiling range hydrocarbons which comprises, in combination, an elongated substantially vertical cylindrical reactor vessel, a horizontal grid means positioned across a bottom cross-sectional portion of the vessel above a bottom semicircular closure member of the vessel, a plurality of vertical heat exchanger tubes positioned within a lower portion of the vessel with the bottom of the tubes spaced vertically above the grid means, a plurality of vertical open end baffle tubes slotted in the wall thereof throughout substantially the entire length thereof positioned interspersed with and adjacent to said heat exchange tubes and spaced horizontally from one another and from said heat exchange tubes to maintain a reactant hydraulic diameter of less than 24 inches during contact with a fluid mass of catalyst particles, the bottoms of said baffle tubes spaced vertically above said grid means, conduit means for withdrawing particles of catalyst from the space intermediate the grid means and the bottom of said tubes, conduit means for adding particles to an upper portion of a bed of fluid catalyst in which said heat exchange means is immersed, a plurality of cyclone separating means located in an upper portion of said vessel provided with dipleg means extending downward through said vessel and terminating in the space above said grid means, a plenum chamber in the upper portion of said vessel in open communication with said cyclone separating means and conduit withdrawal means for reaction products connected to the upper portion of said plenum chamber, an open end conduit means extending from a bottom portion of said vessel beneath said grid means to an upper level of said vessel above said heat exchange and baffle tubes and terminating above the upper interface of a fluid bed of catalyst in the lower portion of the vessel, means for introducing separately controlled gases to the bottom of said open end conduit means, means for charging reactant to said vessel beneath said grid means for flow upwardly through said vessel.

2. The apparatus of claim 1 wherein the vertical heat exchange tubes and said open end slotted baffle tubes are sized in diameter and horizontally positioned with respect to one another to maintain a hydraulic diameter relationship therein within the range of 4 to 8 inches during contact between vaporous material and fluid particles of catalyst.

3. The apparatus of claim 1 wherein the vertical heat exchange tubes are separated into a plurality of tube bundles which can be separately controlled for flow by liquid therethrough or removal from said vessel.

4. The apparatus of claim 1 wherein the tubes are 4 inch diameter tubes and the axis of the tubes is aligned with the cross marks of a 6 inch grid pattern in the vessel cross-section.

5. The apparatus of claim 1 wherein the tubes are grouped into 36 inch square bundles, each bundle comprising 4 steam tubes and 32 baffle tubes.

* * * * *

UNITED STATES PATENT AND TRADEMARK OFFICE
CERTIFICATE OF CORRECTION

PATENT NO. : 4,251,484

DATED : February 17, 1981

INVENTOR(S) : Nicholas Daviduk and James H. Haddad

It is certified that error appears in the above—identified patent and that said Letters Patent is hereby corrected as shown below:

Col. 12, line 31    change "29.9" to -- 29.2 --

Col. 14, line 42    change "by " to -- of --

Signed and Sealed this

Second Day of March 1982

[SEAL]

Attest:

Attesting Officer

GERALD J. MOSSINGHOFF

Commissioner of Patents and Trademarks